US012193937B2

United States Patent
Vaughan

(10) Patent No.: US 12,193,937 B2
(45) Date of Patent: *Jan. 14, 2025

(54) TENSION MANAGEMENT DEVICES FOR STENTED PROSTHESIS DELIVERY DEVICE

(71) Applicant: Medtronic Vascular, Inc., Santa Rosa, CA (US)

(72) Inventor: Brendan Vaughan, Miltown Malbay (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 98 days.

This patent is subject to a terminal disclaimer.

(21) Appl. No.: 18/132,925

(22) Filed: Apr. 10, 2023

(65) Prior Publication Data

US 2023/0240851 A1  Aug. 3, 2023

Related U.S. Application Data

(63) Continuation of application No. 16/941,158, filed on Jul. 28, 2020, now Pat. No. 11,648,121, which is a
(Continued)

(51) Int. Cl.
*A61F 2/24* (2006.01)
*A61F 2/95* (2013.01)
(Continued)

(52) U.S. Cl.
CPC .......... *A61F 2/2466* (2013.01); *A61F 2/2439* (2013.01); *A61F 2/95* (2013.01);
(Continued)

(58) Field of Classification Search
CPC .... A61F 2/2412; A61F 2/2439; A61F 2/2466; A61F 2/95; A61F 2/9517;
(Continued)

(56) References Cited

U.S. PATENT DOCUMENTS 9,510,947 B2  12/2016  Straubinger et al.
9,795,479 B2  10/2017  Lim et al.
(Continued)

FOREIGN PATENT DOCUMENTS

CN    105769387 A    7/2016
CN    105853033 A    8/2016
(Continued)

OTHER PUBLICATIONS

Chen, Xiang, et al., "A novel balloon-expandable valved stents for transcatheter aortic valve implantation: preparation and testing," Academic Journal of Second Military Medical University, vol. 34, No. 7, pp. 764-768 (Jul. 2013).
(Continued)

*Primary Examiner* — Robert A Lynch
(74) *Attorney, Agent, or Firm* — Wentsler LLC

(57) ABSTRACT

Delivery devices and methods for delivering a stented prosthesis to a target site are disclosed. Disclosed delivery devices include a handle assembly including an actuator, an inner shaft assembly interconnected to the handle assembly, and are configured to releasably retain the stented prosthesis to the delivery device with at least one elongate tension member. The delivery devices further include a tension management device that is configured to limit the amount of tension that can be applied via the actuator to the at least one tension member. Certain embodiments are configured to apply different tension limits to different tension members that are controlled by a one or more actuators. Other various embodiments include one or more tension adjustors to selectively adjust one or more tension limits.

19 Claims, 8 Drawing Sheets

Related U.S. Application Data continuation of application No. 15/916,900, filed on Mar. 9, 2018, now Pat. No. 10,772,727.

(60) Provisional application No. 62/469,111, filed on Mar. 9, 2017.

(51) Int. Cl.
*G01L 5/00* (2006.01)
*G01L 5/04* (2006.01)

(52) U.S. Cl.
CPC ............ *G01L 5/0061* (2013.01); *G01L 5/045* (2013.01); *A61F 2/2412* (2013.01); *A61F 2/9517* (2020.05)

(58) Field of Classification Search
CPC ......... A61F 2002/9511; F16H 19/0672; G01L 5/0061; G01L 5/045
See application file for complete search history.

(56) References Cited

U.S. PATENT DOCUMENTS

| | | | |
|---|---|---|---|
| 10,004,599 B2 | 6/2018 | Rabito et al. |
| 10,016,275 B2 | 7/2018 | Nyuli et al. |
| 10,098,734 B2 | 10/2018 | Hoang |
| 10,179,047 B2 | 1/2019 | Lee et al. |
| 10,307,251 B2 | 6/2019 | Straubinger et al. |
| 10,624,640 B2 | 4/2020 | Dell et al. |
| 10,772,727 B2 | 9/2020 | Vaughan |
| 10,779,935 B2 | 9/2020 | Scorsin et al. |
| 10,966,850 B2 | 4/2021 | Irwin et al. |
| 11,648,121 B2 * | 5/2023 | Vaughan ............... A61F 2/2466 623/2.11 |
| 2005/0197692 A1 | 9/2005 | Pai et al. |
| 2007/0233223 A1 | 10/2007 | Styrc |
| 2013/0110227 A1 | 5/2013 | Quadri et al. |
| 2014/0114390 A1 | 4/2014 | Tobis et al. |
| 2015/0238315 A1 | 8/2015 | Rabito et al. |
| 2015/0265442 A1 | 9/2015 | Styrc |
| 2016/0158010 A1 | 6/2016 | Lim et al. |
| 2016/0262741 A1 | 9/2016 | Gilmore et al. |

FOREIGN PATENT DOCUMENTS

| | | |
|---|---|---|
| CN | 105943212 A | 9/2016 |
| EP | 2832318 A1 | 2/2015 |
| WO | 2016014558 A1 | 1/2016 |

OTHER PUBLICATIONS

International Search Report and Written Opinion from related PCT Application No. PCT/US2018/021761, mailed Jun. 5, 2018, 11 pages.

\* cited by examiner

TENSION MANAGEMENT DEVICES FOR STENTED PROSTHESIS DELIVERY DEVICE

CROSS-REFERENCE TO RELATED APPLICATIONS

This application is a continuation of U.S. application Ser. No. 16/941,158, filed on Jul. 28, 2020, which is a continuation of U.S. application Ser. No. 15/916,900, filed on Mar. 9, 2018, now U.S. Pat. No. 10,772,727, which claims the benefit of the filing date of U.S. Provisional Patent Application No. 62/469,111, filed Mar. 9, 2017, the entire teachings of which are incorporated herein by reference.

BACKGROUND

This disclosure relates to delivery devices and tension management devices to control and limit the tension applied to at least one elongate tension member compressively retaining a stented prosthesis to the delivery device.

A human heart includes four heart valves that determine the pathway of blood flow through the heart: the mitral valve, the tricuspid valve, the aortic valve, and the pulmonary valve. The mitral and tricuspid valves are atrio-ventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Diseased or otherwise deficient heart valves can be repaired or replaced using a variety of different types of heart valve surgeries. One conventional technique involves an open-heart surgical approach that is conducted under general anesthesia, during which the heart is stopped and blood flow is controlled by a heart-lung bypass machine.

More recently, minimally invasive approaches have been developed to facilitate catheter-based implantation of the valve prosthesis on the beating heart, intending to obviate the need for the use of classical sternotomy and cardiopulmonary bypass. In general terms, an expandable valve prosthesis is compressed about or within a catheter, inserted inside a body lumen of the patient, such as the femoral artery, and delivered to a desired location in the heart where the valve prosthesis is then deployed.

The disclosure presents improvements related to the above.

SUMMARY

The present disclosure relates to delivery devices for stented prosthesis loading, delivery and implantation. Such delivery devices can include an optional outer delivery sheath assembly, an inner shaft assembly and a handle assembly. The delivery devices provide a loaded delivery state in which the stented prosthesis is loaded and compressed over the inner shaft assembly. Compression of the stented prosthesis can be adjusted with one or more elongate tension members, e.g., sutures or the like, which extend around the stented prosthesis and proximately to an actuation and release assembly, which can, in some embodiments, be provided in the handle assembly. The delivery device can be manipulated to adjust tension in the tension members to permit the stented prosthesis to compress, self-expand, and ultimately release from the inner shaft assembly.

Disclosed embodiments further include a tension management device to maintain the necessary tension in one or more tension members (i.e. compression of the stented prosthesis) while also preventing the over tensioning of tension members to the point of damage or failure, which could compromise the procedure. In various embodiments, the tension management device is configured to limit the tension that can be applied to one or more tension members having differing predetermined tension limits. In further embodiments, the tension management device can adjust or toggle between varying tension limits for the one or more tension members. The disclosed embodiments result in a user friendly device that likely increases user confidence and is believed to reduce the risk associated with transcatheter stented prosthesis delivery procedures utilizing elongate tension members for retaining the stented prosthesis on the delivery device.

DETAILED DESCRIPTION

Specific embodiments of the present disclosure are now described with reference to the figures, wherein like reference numbers indicate identical or functionally similar elements.

Figure 1:
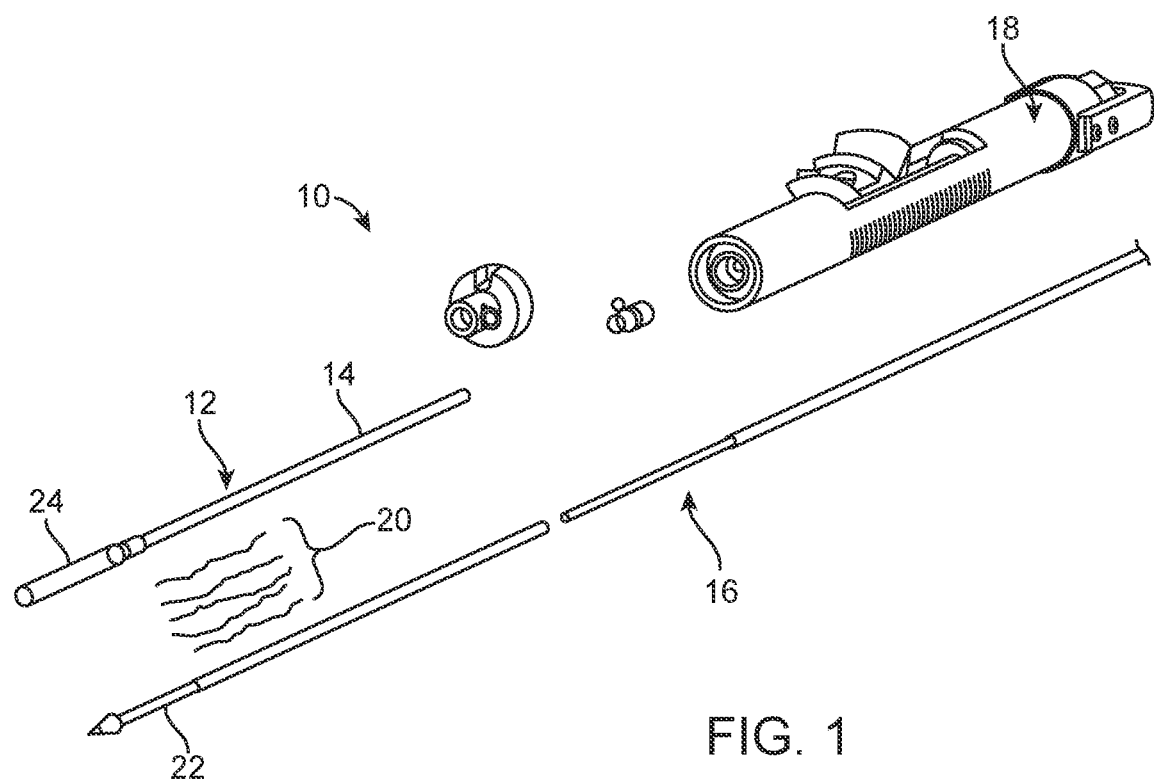
FIG. 1 is a perspective view of an example of a delivery device for delivering a stented prosthesis.
Figure 2A:
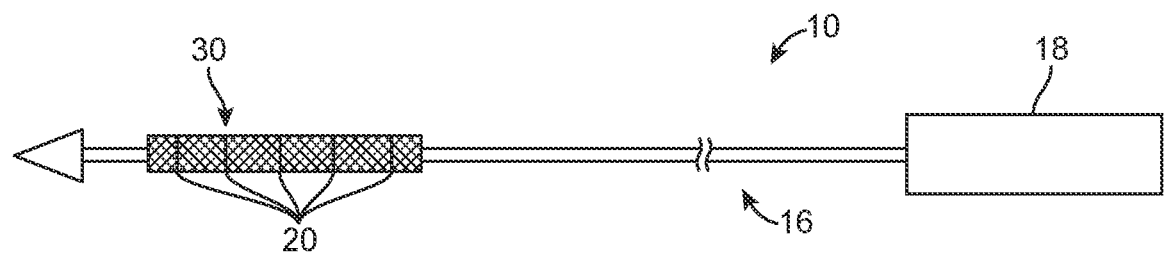
FIG. 2A is a schematic illustration of the delivery device of FIG. 1 having the stented prosthesis positioned over an inner shaft assembly of the delivery device in a compressed arrangement with a plurality of elongate tension members.
Figure 2B:
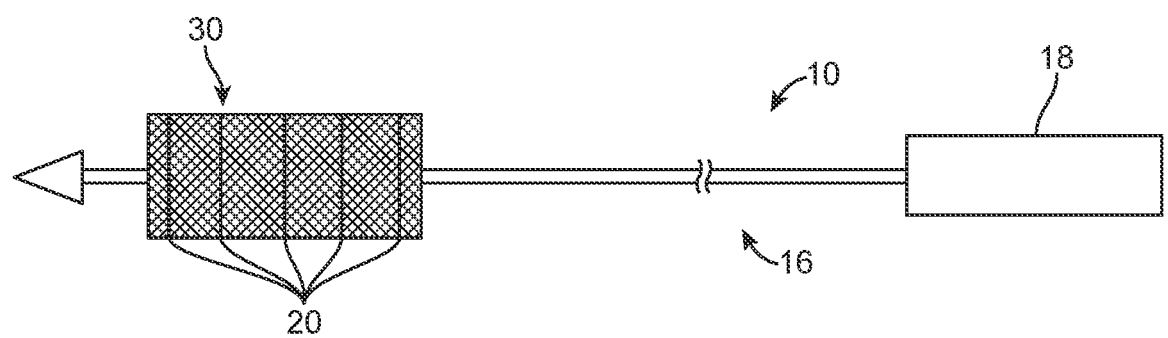
FIG. 2B is a schematic illustration of the delivery device of FIG. 2A having the stented prosthesis positioned over the inner shaft assembly of the delivery device in an expanded arrangement with the plurality of elongate tension members.

As described below, aspects of the present disclosure relate to delivery devices utilizing one or more elongate tension members (e.g., sutures, chords, wires or filaments) to retain a stented prosthesis for delivery to a target site. By way of background, general components of one non-limiting example of a delivery device 10 with which some embodiments of the present disclosure are useful are illustrated in FIGS. 1-2B. The delivery device 10 is arranged and configured for percutaneously delivering a stented prosthesis. For example, the stented prosthesis can be a stented prosthetic heart valve 30 (schematically illustrated, hereinafter "prosthetic valve"). The delivery device 10 includes an optional outer sheath assembly 12 having an outer sheath 14, an inner shaft assembly 16 and a handle assembly 18. One or more elongate tension members 20 are provided, and can be considered part of the delivery device 10 in some embodiments or as part of the prosthetic valve 30 in other embodiments. The delivery device 10 provides a loaded, compressed arrangement (FIG. 2A) in which the prosthetic valve 30 is loaded over and is compressively retained on a spindle 22 of the inner shaft assembly 16 by the tension members 20. As is schematically illustrated in FIGS. 2A-2B, compression of the prosthetic valve 30 is adjustable by varying the tension in the one or more tension members 20. In this embodiment, the outer sheath 14 is interconnected to a capsule 24 that is selectively disposed over the compressed prosthetic valve 30 and assists in constraining the prosthetic valve 30. Once loaded, compressed and optionally sheathed by the capsule 24, the prosthetic valve 30 is delivered to the target site. When the prosthetic valve 30 is at the target site, the capsule 24 is withdrawn and tension in the tension members 20 is lessened or released to permit the prosthetic valve 30 to self-expand to an expanded arrangement, partially releasing and ultimately fully deploying the prosthetic valve 30 from the inner shaft assembly 16 (see, FIG. 2B). Movement of the outer sheath 14 and capsule 24 relative to the prosthetic valve 30 can be actuated by the handle assembly 18. The present disclosure focuses on numerous ways to incorporate a tension management device into a delivery device, such as the delivery device 10. As will be discussed in detail below, the disclosed tension management devices are arranged and configured to maintain and limit the tensioning force that can be transferred to the one or more tension members 20

As referred to herein, stented prostheses and stented prosthetic heart valves useful with the various devices and methods of the present disclosure may assume a wide variety of configurations, such as a bioprosthetic heart valve having tissue leaflets or a synthetic heart valve having polymeric, metallic or tissue-engineered leaflets, and can be specifically configured for replacing valves of the human heart. The stented prostheses and prosthetic valves of the present disclosure may be self-expandable, balloon expandable and/or mechanically expandable or combinations thereof. In general terms, the prosthetic valves of the present disclosure include a stent or stent frame having an internal lumen maintaining a valve structure (tissue or synthetic), with the stent frame having a normal, expanded condition or arrangement and collapsible to a compressed condition or arrangement for loading within the delivery device. For example, the stents or stent frames are support structures that comprise a number of struts or wire segments arranged relative to each other to provide a desired compressibility and strength to the prosthetic valve. The struts or wire segments are arranged such that they are capable of self-transitioning from, or being forced from, a compressed or collapsed arrangement to a normal, radially expanded arrangement. The struts or wire segments can be formed from a shape memory material, such as a nickel titanium alloy (e.g., Nitinol™). The stent frame can be laser-cut from a single piece of material, or can be assembled from a number of discrete components.

Figure 3A:
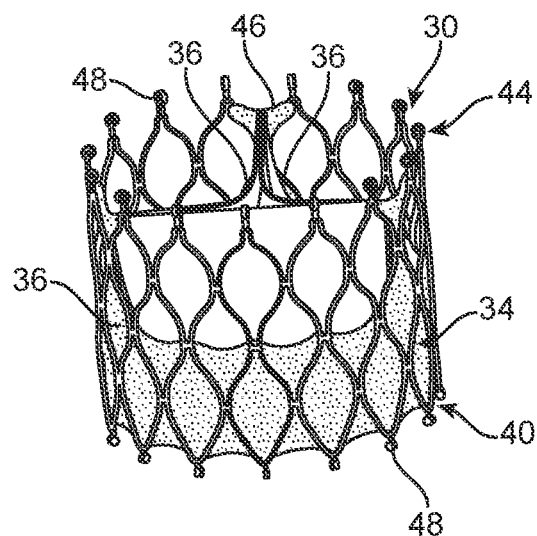
FIG. 3A is a perspective view of a stented prosthetic heart valve that can be used with the delivery devices disclosed herein shown in the expanded arrangement.
Figure 3B:
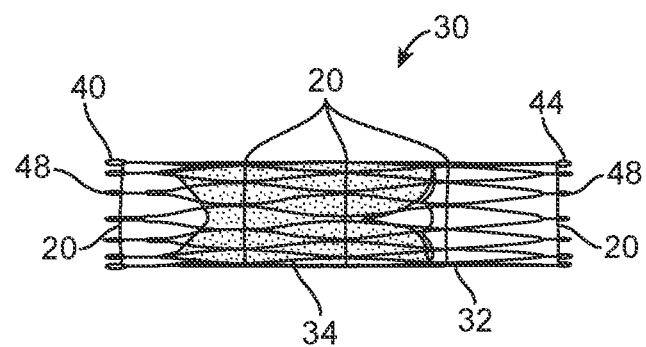
FIG. 3B is a front view of the stented prosthetic heart valve of FIG. 3A in the compressed arrangement.
Figure 4:
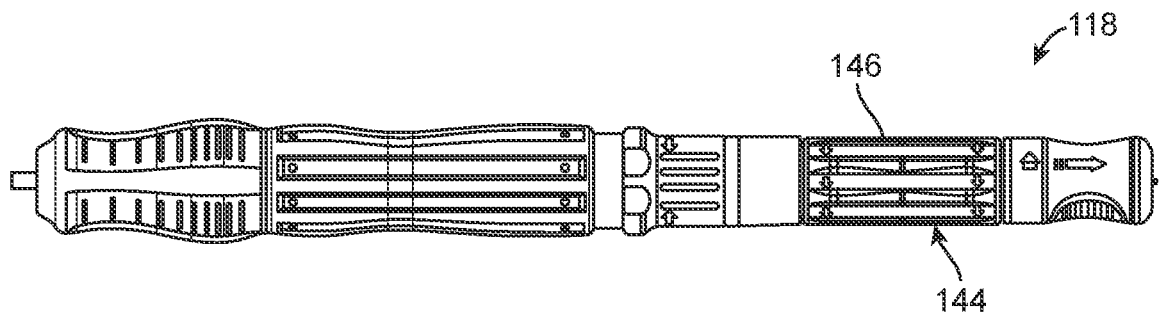
FIG. 4 is a side view of one handle assembly having a tension management device that can be used with a delivery device, such as that of FIGS. 1-2B.
Figure 5:
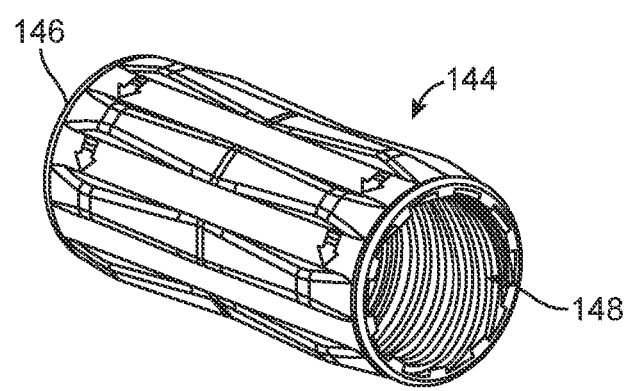
FIG. 5 is a perspective view of an actuator of the handle assembly of FIG. 4.

One non-limiting example of the stented prosthetic valve 30 is illustrated in detail in FIGS. 3A-3B. As a point of reference, the prosthetic valve 30 is shown in a normal or expanded arrangement in the view of FIG. 3A and a compressed arrangement in the view of FIG. 3B. The prosthetic valve 30 includes a stent or stent frame 32 and a valve structure 34. The stent frame 32 can assume any of the forms mentioned above, and is generally constructed to be self-expandable from the compressed arrangement to the normal, expanded arrangement. As discussed above, compression of the prosthetic valve 30 can be achieved with one or more tension members 20.

The valve structure 34 of the prosthetic valve 30 can assume a variety of forms, and can be formed, for example, from one or more biocompatible synthetic materials, synthetic polymers, autograft tissue, homograft tissue, xenograft tissue, or one or more other suitable materials. In some embodiments, the valve structure 34 can be formed, for example, from bovine, porcine, equine, ovine and/or other suitable animal tissues. In some embodiments, the valve structure 34 is formed, for example, from heart valve tissue, pericardium, and/or other suitable tissue. In some embodiments, the valve structure 34 can include or form one or more leaflets 36. For example, the valve structure 34 can be in the form of a tri-leaflet bovine pericardium valve, a bi-leaflet valve, or another suitable valve.

In some prosthetic valve constructions, such as that of FIGS. 3A-3B, the valve structure 34 can comprise two or three leaflets 36 that are fastened together at enlarged lateral end regions to form commissural joints, with the unattached edges forming coaptation edges of the valve structure 34. The leaflets 36 can be fastened to a skirt that in turn is attached to the stent frame 32. The prosthetic valve 30 includes a first end 40 and an opposing second end 44 of the prosthetic valve 30. As shown, the stent frame 32 can have a lattice or cell-like structure, and optionally forms or provides posts 46 corresponding with commissures of the valve structure 34 as well as features 48 (e.g., crowns, eyelets or other shapes) at the first and second ends 40, 44. If provided, the posts 46 are spaced equally around frame 32 (only one post 46 is clearly visible in FIG. 3A).

FIGS. 4-6D collectively illustrate components of an alternate handle assembly 118. The alternate handle assembly 118 can be incorporated into a delivery device, such as that of FIGS. 1-2B. The handle assembly 118 is configured and operates similarly to the handle assembly 18 except as explicitly stated. The handle assembly 118 of this embodiment includes an actuator 144 positioned over and engaged with one tension management device 150, which is connected to one or more tension members 120 positioned around a stented prosthesis as shown in FIGS. 1-2B, for example. The actuator 144 is configured to adjust tension in the tension members 120 via the tension management device 150, while the tension management device 150 further is configured to limit the amount of tensioning force that can be applied to the tension members 120. In one example embodiment, the actuator 144 translates rotational force of the actuator 144 to an actuator gear 156 of the tension management device 150 to selectively tension or release the tension in the tension members 120. In this example embodiment, the actuator 144 includes a generally cylindrical body 146 having a threaded interior surface 148. The tension management device 150 can include a housing 152, the actuator gear 156, a drive gear 158, a reel 160 and biasing element 162 (e.g., one or more pre-compressed springs, alternate resilient element or the like). Each of the actuator gear 156 and the drive gear 158 are positioned within the same plane and include a plurality of interlocking teeth 164, 166 (generally referenced). In this embodiment, the teeth 164 of the actuator gear 156 are angled with respect to a rotational axis of the actuator gear 156 to match the pitch of the threaded interior surface 148 of actuator 144. A few of the actuator gear teeth 164 are exposed with respect to an opening 154 in the housing 152 to enable engagement of actuator gear teeth 164 with the interior threaded surface 148 of the actuator 144. In this way, rotation of the actuator 144 in one direction (e.g., clockwise), subsequently rotates the actuator gear 156 about its axis, which correspondingly rotates the drive gear 158 about its axis. In conditions where the tension member tension limit is not met, the reel 160 is engaged with the drive gear 158 such that rotation of the drive gear 158 correspondingly rotates the reel 160. For example, one or more tension members 120 can be secured within a channel 170 of a reel 160 so that as the reel 160 rotates, the tension member(s) 120 are wound and unwound around the reel 160 to correspondingly compress and expand the prosthetic valve (not shown) as the tension in the tension member(s) 120 is varied. In embodiments where more than one elongate tension member is used to compresses the stented prosthesis, a plurality of tension members can individually be connected to one or more respective reels or a plurality of tension members can be secured to one elongate tension member that is connected to a reel.

Figure 6A:
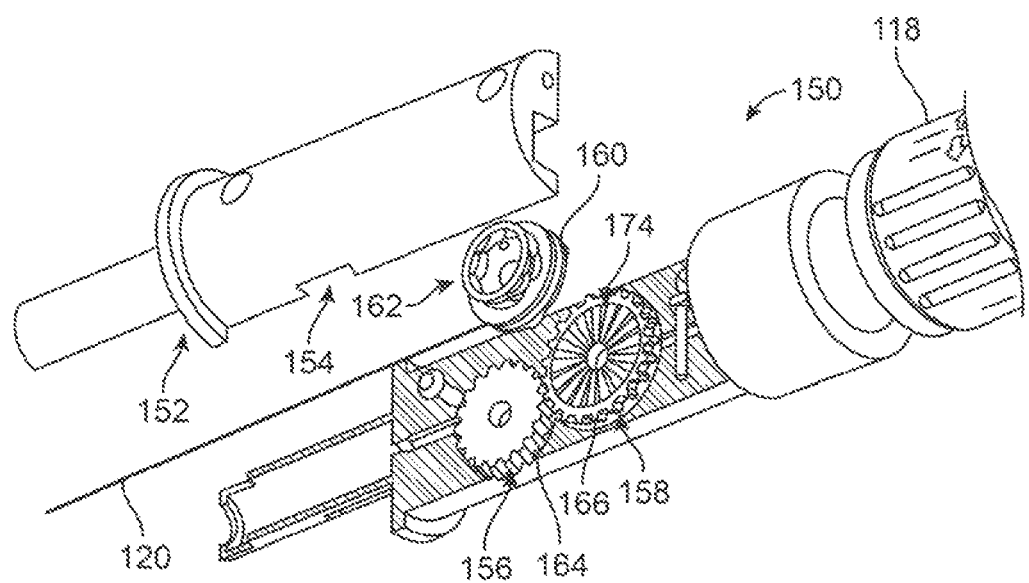
FIG. 6A is a partially exploded, first side view of a tension management device incorporated into the handle assembly of FIG. 4.
Figure 6B:
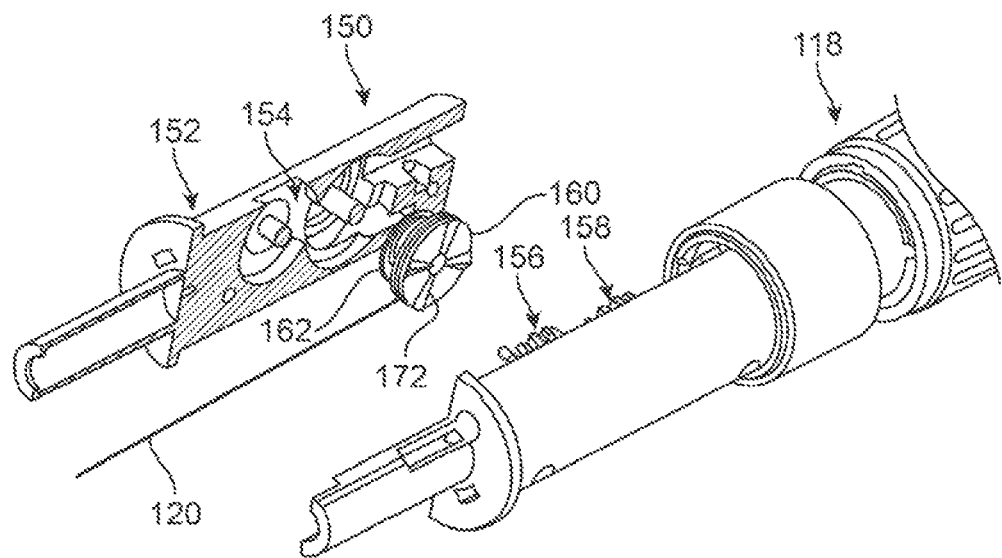
FIG. 6B is a partially exploded, second side view of the tension management device of FIG. 6A.
Figure 6C:
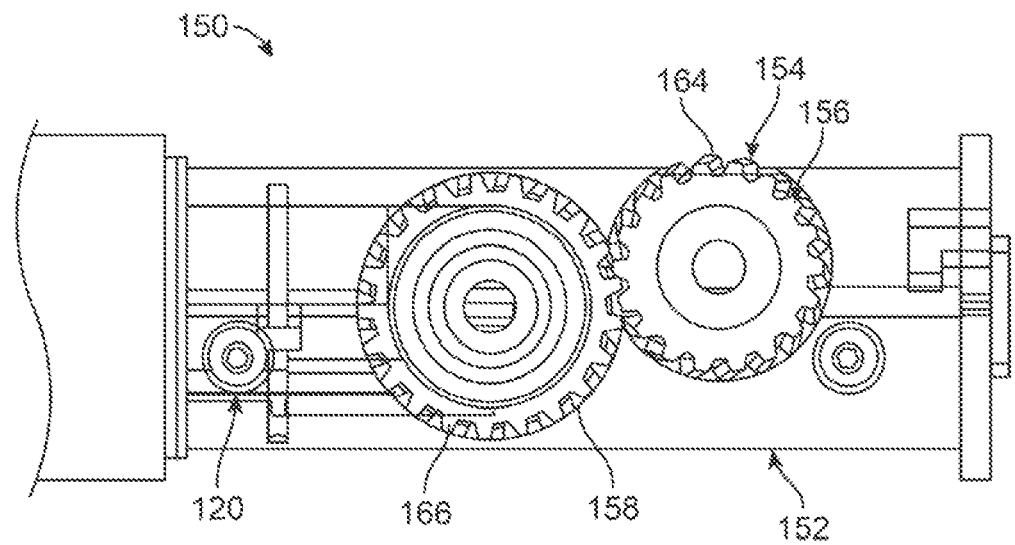
FIG. 6C is a partial top view of the assembled tension management device of FIGS. 4 and 6A-6B (a housing of the tension management device is shown as transparent for ease of illustration).
Figure 6D:
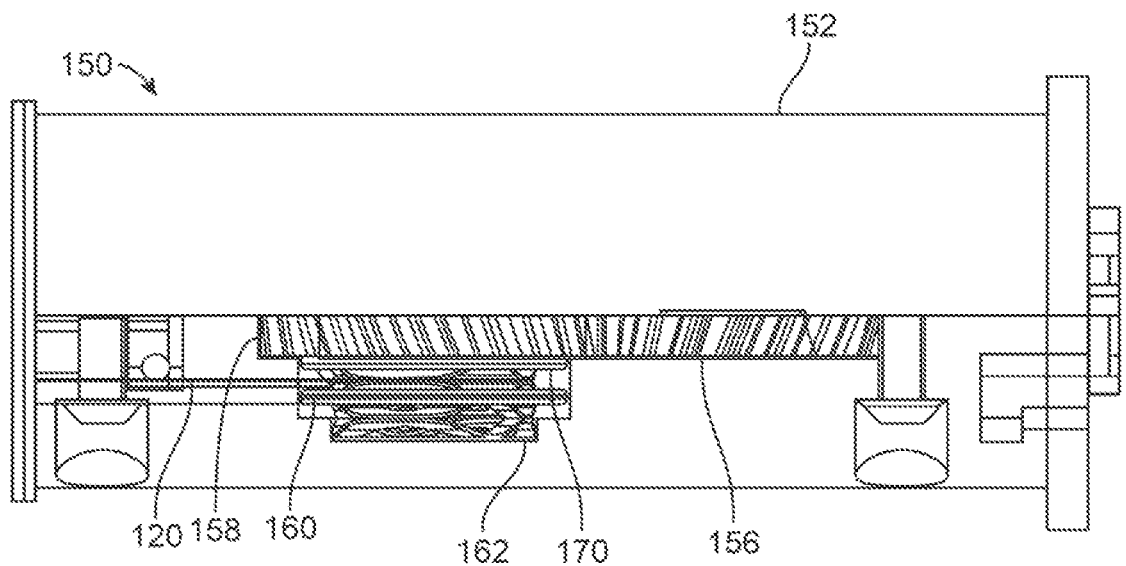
FIG. 6D is a partial side view of the assembled tension management device of FIGS. 4 and 6A-6C (the housing of the tension management device is shown as transparent for ease of illustration).

The amount of tension that can be applied to compresses the stented prosthesis with the tension member(s) 120 (i.e. the tension limit) is dictated via the selection of the biasing element 162, which is positioned opposite the drive gear 158, between the reel 160 and the housing 152. The biasing element 162 biases the reel 160 in the direction of the drive gear 158 to urge at least one tooth 172 (referenced generally) of the reel 160 to engage one or more pockets 174 (referenced generally) in the drive gear 158 so that rotation of the drive gear 158 directly translates to rotation of the reel 160. As best shown in FIG. 6A, the drive gear 158 can optionally include a generally turbine-shaped face defining generally wedge-shaped pockets 174. The drive gear 158 and reel 160 interface can include, for example, four teeth 172 symmetrically positioned around the reel 160 that can respectively engage one of sixteen pockets 174 in the drive gear 158 to engage the reel 160. In one example embodiment, each tooth 172 has a generally triangular cross-section. The biasing element 162 is selected to provide a biasing force such that the reel 160 engages drive gear 158 in conditions where the tension in the tension member(s) 120 is under the predetermined limit but where the reel 160 slips and disengages the drive gear 158 in conditions where the tension meets or exceeds the predetermined limit due to compression of the biasing element 162. The displacement, or movement in which the teeth 172 of the reel 160 slip and disengage from the pockets 174 of the drive gear 158 can be about 1 mm, for example.

Figure 7A:
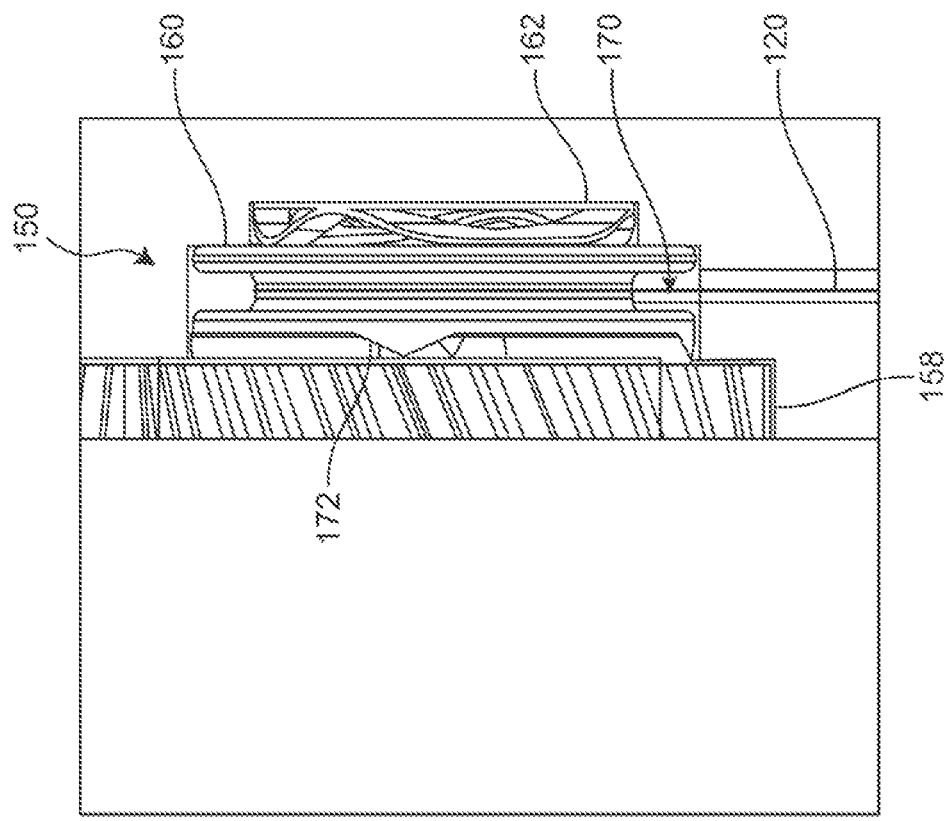
FIG. 7A is an enlarged view of select components of the tension management device of FIGS. 4 and 6A-6D illustrating a reel biased with a biasing element such that it engages a drive gear when tension in a respective tension member is below a predetermined limit.
Figure 7B:
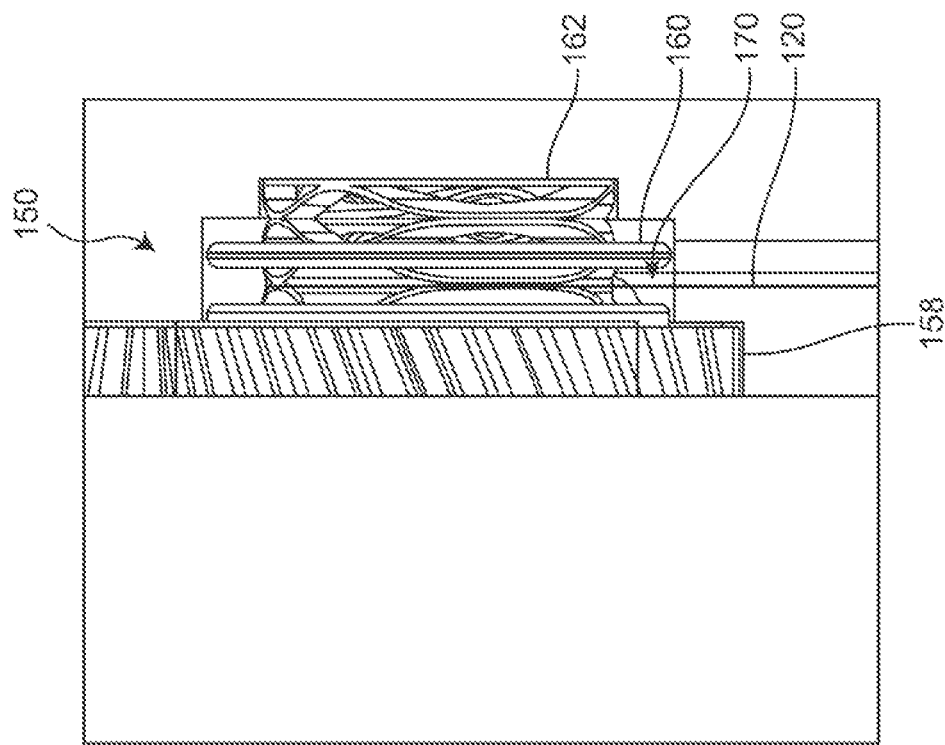
FIG. 7B is an enlarged view of select components of the tension management device of FIGS. 4 and 6A-7A illustrating the reel disengaged with the drive gear, against the bias of the biasing element, when the tension in the respective tension member exceeds the predetermined limit.

FIG. 7A illustrates the tension management device 150 in operating conditions where the tension applied to the elongate tension member(s) 120 is under the predetermined tension limit. In this condition, the teeth 172 of the reel 160 are engaged with pockets 174 of the drive gear 158. Once the maximum tension force is achieved, as shown in FIG. 7B, the biasing element 162 sufficiently compresses such that the reel teeth 172 disengage from the drive gear 158, against the bias of the biasing element 162 so that any rotation of the drive gear 158 is not transferred to the reel 160. In this condition, tension is maintained in the tension member(s) 120 but no additional force is applied by rotation of the drive gear 158 (i.e. even if the actuator 144 and actuator gear 156 continue to drive and rotate the drive gear 158). Therefore, when the biasing element 162 is disengaged from the drive gear 158, the reel 160 remains stationary and does not release tension in the at least one tension member 120. In certain embodiments, an audible click is provided once the reel 160 disengages the drive gear 158 to alert the user that the limit has been met. The audible click can be provided, for example, as a byproduct of the reel 160 slipping relative to the drive gear 158 due to the compression loaded on to the reel 160 during the slip of the reel 160 audibly clicks as it returns to the engaged state with the drive gear 158. In this configuration, the audible click continues during use as the reel 160 disengages and engages with the drive gear 158. In various embodiments, the tension is preselected, via selection of the biasing element 162, to limit the applied tension to a force of about 90 N to about 100 N, for example.

Figure 8A:
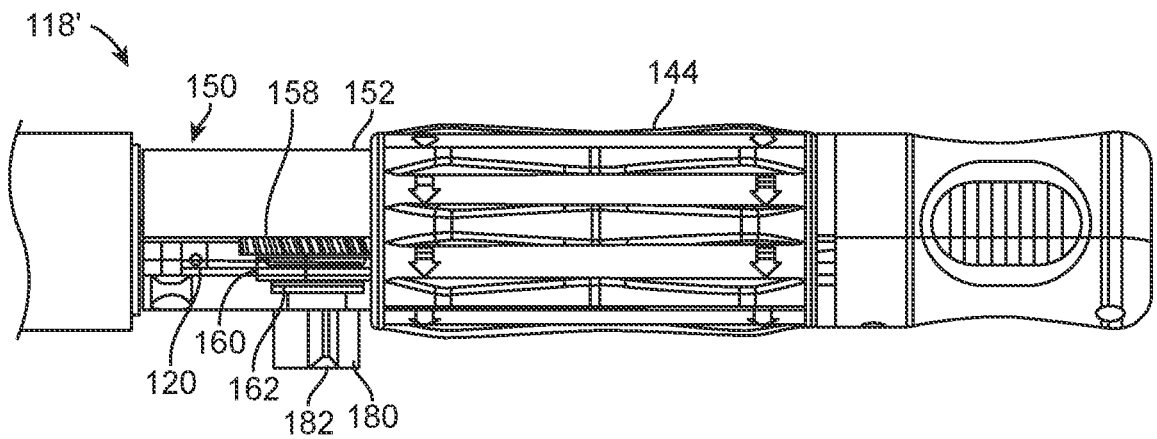
FIG. 8A is a partial, side view of an alternate handle assembly having a tension management device including a toggle switch configured to adjust the predetermined tension limit of at least one tension member connected to a reel of the tension management device (a housing of the tension management device is shown as transparent for ease of illustration).
Figure 8B:
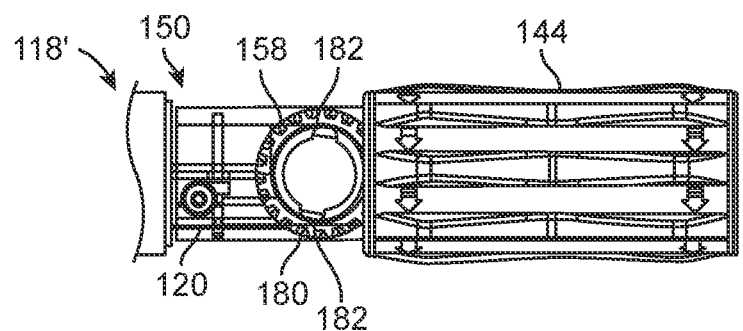
FIG. 8B is a partial, side view of the handle assembly of FIG. 8A showing the toggle switch in a first position (wherein the housing is shown as transparent for ease of illustration).
Figure 8C:
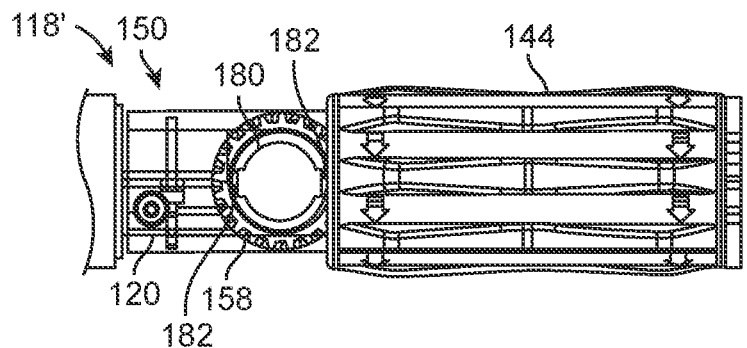
FIG. 8C is a partial, side view of the handle assembly of FIGS. 8A-8B showing the toggle switch in a second position (wherein the housing is shown as transparent for ease of illustration).

FIGS. 8A-8C illustrate an alternate handle assembly 118', which is substantially similar to the handle assembly 118 disclosed above but further includes an optional tension limit adjuster 180 that can be incorporated into tension management devices 150, 250, 350 disclosed herein to adjust or select the tension limit of the tension management device. Tension adjuster 180 can be useful, for example, when different tension limits are desired during stented prosthesis loading and deployment procedures. For example, in one embodiment, tension adjuster 180 can function as a toggle switch for dictating the tension limit setting of the tension management device 150. In the illustrated embodiment, the tension adjuster 180 includes a two opposing tabs 182 that a user can grip to rotate the adjuster 180 in two positions (FIGS. 8B-8C). In each of the two positions, the adjuster 180 varies the compression of the biasing element 162, thus adjusting the bias on the reel 160, which correspondingly adjusts the maximum tension that can be transferred to the at least one tension member 120 connected to the respective reel 160. It is envisioned that other similar ways of varying the compression of the reel 160 are possible.

Figure 9:
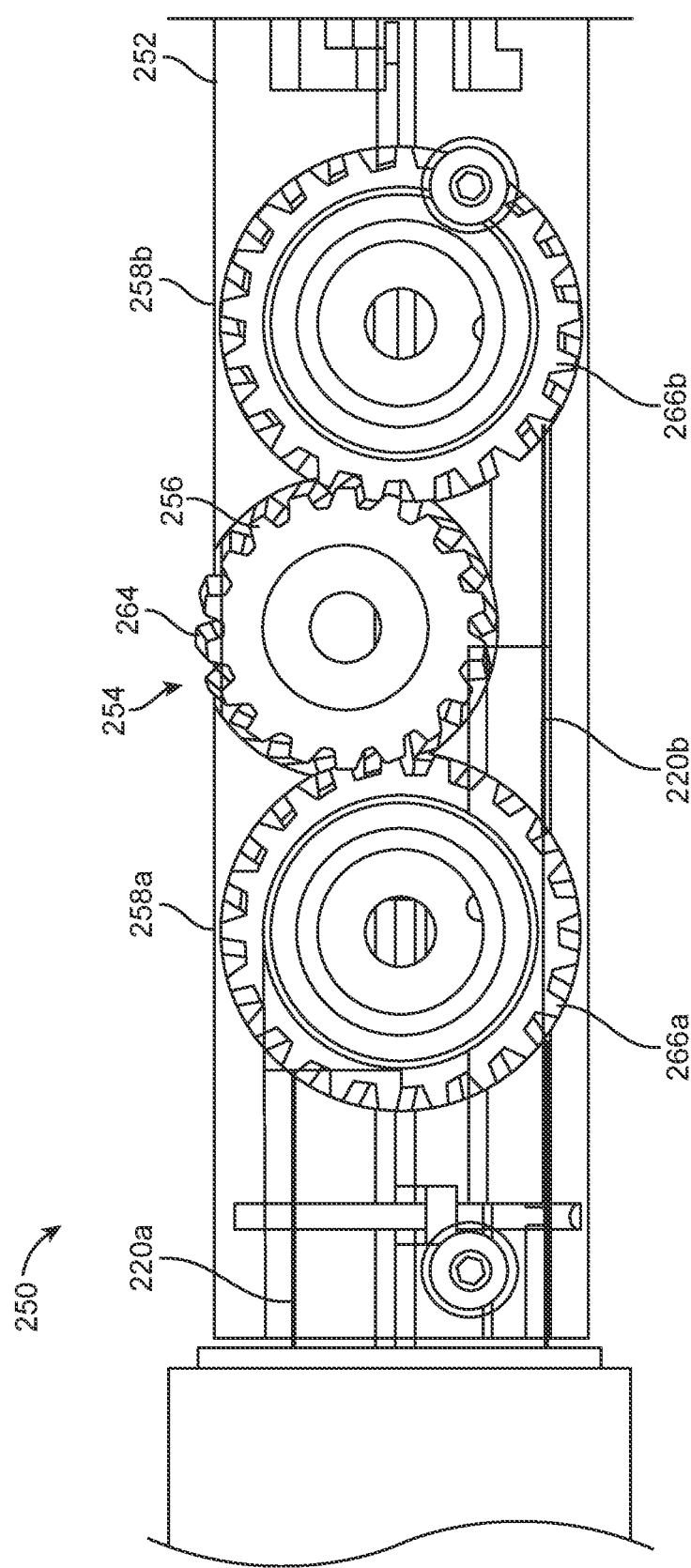
FIG. 9 is a top view of an alternate tension management device (having a housing shown as transparent for ease of illustration).

FIG. 9 illustrates an alternate tension management device 250 that is substantially similar to that of FIGS. 4 and 6A-7B. In this embodiment, the tension management device 250 includes a housing 252 (shown as partially transparent for clarity) having a window or opening 254. The tension management device 250 further includes an actuator gear 256 having at least some teeth 264 exposed with respect to the opening 254 to engage the associated actuator of the handle assembly (e.g., actuator 144 of FIGS. 4-5). The actuator gear teeth 264 are further engaged with the respective teeth 266a, 266b of two drive gears 258a, 258b. As with prior disclosed embodiments, each drive gear 258a, 258b is connected to a respective reel biased toward the respective drive gear 258a, 258b with a biasing element. In this configuration, at least two tension members 220a, 220b retain the stented prosthesis on the delivery device and are controllable via a single actuator (e.g., actuator 144). A first elongate tension member 220a is interconnected to a first reel and a second elongate tension member 220b is interconnected to a second reel. The first and second reels, as well as corresponding biasing elements, are positioned below the respective drive gears 258a, 258b and not visible in FIG. 9 but can be configured in the same way as the drive gear 158, reel 160 and biasing element 162 of FIGS. 7A-7B. In this embodiment, the tension members 220a, 220b are reeled in differing directions managed by opposing reel starting positions. Similar to the prior embodiments, during operating conditions where the tension applied to the tension members 220a, 220b is under the predetermined limit, each reel is engaged with the drive gear 258a, 258b via one or more respective teeth (e.g., teeth 172 of FIG. 7B). Once the maximum force is achieved, the respective reel disengages from the respective drive gear 258a, 258b such that the tension is maintained in the respective tension member(s) 220a, 220b, but no additional tensioning force is applied to the respective tension member(s) 220a, 220b even if the respective drive gear 258a, 258b continues to rotate (e.g., even if the actuator gear 256, via an actuator such as actuator 144, continues to drive one or more of the drive gears 258a, 258b). In some embodiments, the predetermined tension limit differs for the first and second reels, meaning that one reel can be engaged with the respective drive gear 258a, 258b when the second reel is not. As discussed above, the tension limit for each reel can differ by selecting the biasing element to provide the desired biasing force or by use of a tension adjuster to adjust the compression of the biasing element to provide the desired biasing force. In certain embodiments, an audible click, as described above, is provided once each reel disengages from the respective drive gear 258a, 258b to alert the user that the tension limit has been met. It is envisioned that more than two reels can be actuated by the actuator gear 256 in alternate embodiments. It is further envisioned that the delivery device can include one or more reels actuated by one or more respective actuators and/or one or more actuator gears connected to one or more respective actuators.

Figure 10:
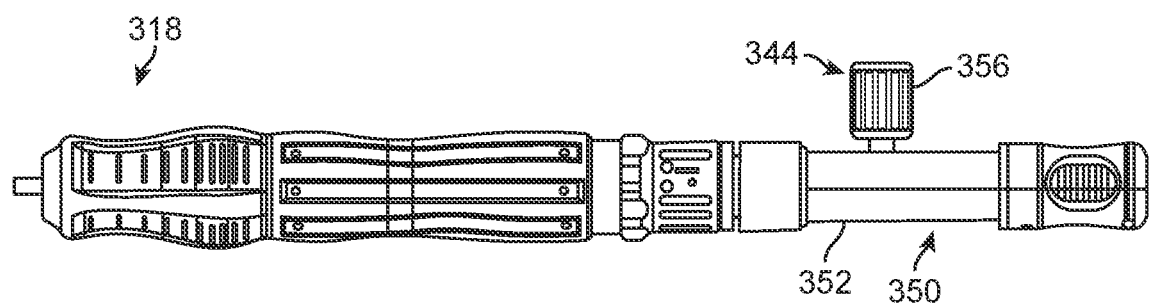
FIG. 10 is a side view of an alternate handle assembly having a tension management device that can be used with a delivery device, such as that of FIGS. 1-2B.
Figure 11:
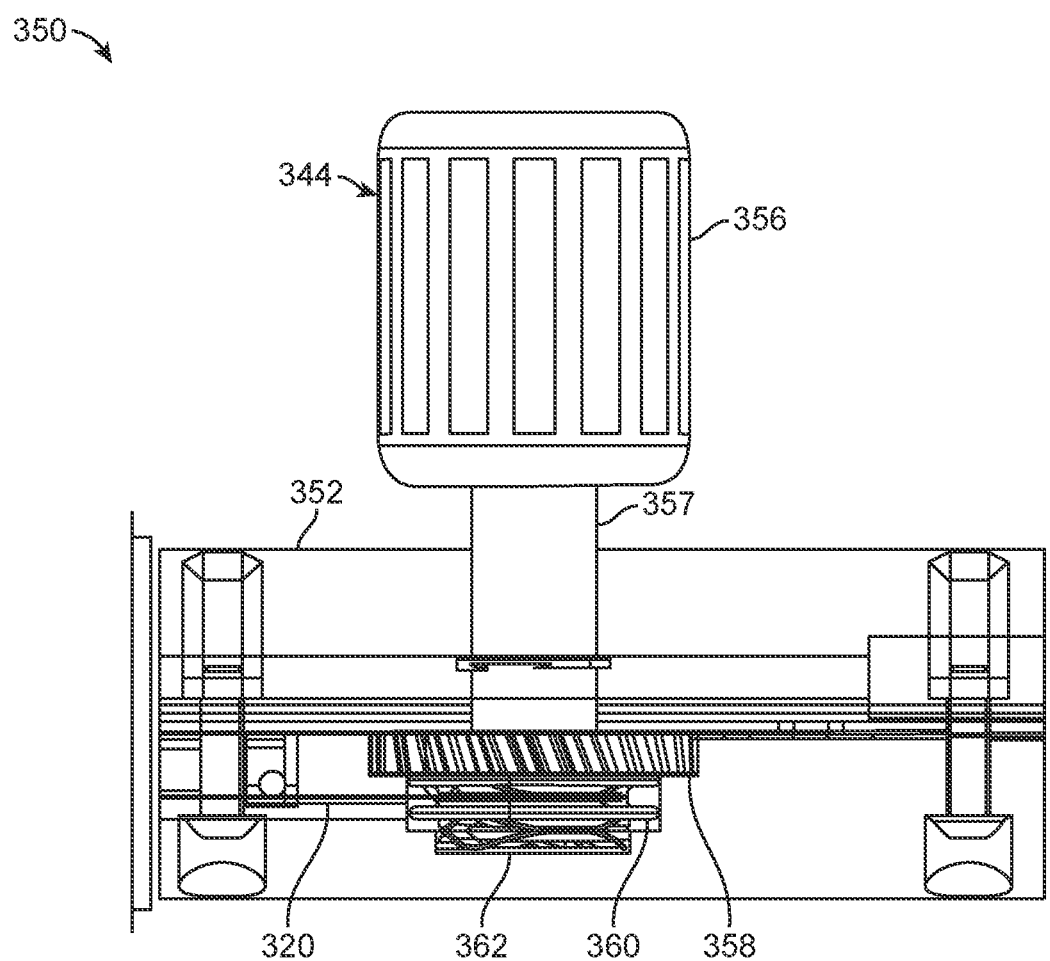
FIG. 11 is a partial, side view of an alternate actuator engaging a drive gear of the tension management device of FIG. 10 (a housing of the tension management device is shown as transparent for ease of illustration).

One alternate handle assembly 318 including an alternate tension management device 350 having an alternate actuator 344 is illustrated in FIGS. 10-11. In this embodiment, the actuator 344 includes a rotatable knob 356 fixed to a shaft 357 that extends through housing 352. The actuator gear of prior embodiments is omitted and the shaft 357 of the actuator 344 is directly connected to a drive gear 358. Rotation of the knob 356 in either the clockwise or counterclockwise direction applies corresponding 1:1 rotation of the shaft 357 and the drive gear 358, which subsequently rotates a corresponding reel 360, thus winding or unwinding tensioning member(s) 320 on the reel 360 to further tension or release tension in the tensioning member(s) 320, respectively. The reel 360 is biased toward the drive gear 358 with a biasing element 362, which functions as disclosed with respect to the biasing elements of prior embodiments. The actuator 344 can be incorporated into all embodiments disclosed herein, as desired.

Although the present disclosure has been described with reference to preferred embodiments, workers skilled in the art will recognize that changes can be made in form and detail without departing from the spirit and scope of the present disclosure.

What is claimed is:

1. A delivery device comprising:
at least one tension member;
a handle assembly comprising an actuator configured to adjust a tension in the at least one tension member;
an inner shaft assembly interconnected to the handle assembly; and
a tension management device comprising a first drive gear rotatable about a first axis and a first reel rotatable about the first axis to wind the at least one tension member around the first reel, and the first reel and the first drive gear are biased together into engagement in a direction of the first axis, wherein rotating the actuator causes the first drive gear to rotatably disengage from the first reel when a tension in the at least one tension member is above a predetermined tension limit.

2. The delivery device of claim 1, wherein the first reel and the first drive gear are biased into engagement with an axial face of the first reel engaging an axial face of the first drive gear and the axial faces of the first reel and the first drive gear are each perpendicular to the first axis.

3. The delivery device of claim 1, wherein the first reel comprises a tooth that engages the first drive gear.

4. The delivery device of claim 3, wherein the tooth of the first reel is configured to engage a pocket in the first drive gear to achieve the biased engagement of the first drive gear and the first reel.

5. The delivery device of claim 1, wherein a rotation of the actuator is configured to rotate an actuator gear, and a rotation of the actuator gear is configured to rotate the first drive gear.

6. The delivery device of claim 5, wherein the actuator comprises a generally cylindrical body comprising a threaded inner surface engaging with teeth of the actuator gear, wherein a rotation of the actuator is configured to rotate the actuator gear by the engagement between the threaded inner surface of the actuator and the teeth of the actuator gear.

7. The delivery device of claim 5, wherein the actuator gear and the first drive gear are positioned within the same plane.

8. The delivery device of claim 1, further comprising a capsule configured to sheath a compressed prosthetic heart valve after the prosthetic heart valve is compressed onto the inner shaft assembly with the at least one tension member.

9. The delivery device of claim 1, wherein the at least one tension member comprises a first tension member and a second tension member, and the actuator is configured to adjust a tension in the first tension member and a tension in the second tension member.

10. The delivery device of claim 9, wherein the tension management device further comprises a second drive gear rotatable about a second axis and a second reel rotatable about the second axis, the second reel and the second drive gear are biased together into engagement in a direction of the second axis, the first tension member is configured to be wound around the first reel and the second tension member is configured to be wound around the second reel.

11. The delivery device of claim 10, wherein a rotation of the actuator is configured to rotate an actuator gear, and a rotation of the actuator gear is configured to rotate the first drive gear and the second drive gear.

12. The delivery device of claim 11, wherein the actuator gear, the first drive gear, and the second drive gear are positioned within the same plane.

13. The delivery device of claim 10, wherein a rotation of the actuator is configured to cause the first drive gear to rotatably disengage from the first reel when a tension in the first tension member is above a first predetermined tension limit, and wherein a rotation of the actuator is further configured to cause the second drive gear to rotatably disengage from the second reel when a tension in the second tension member is above a second predetermined tension limit.

14. The delivery device of claim 13, wherein the tension management device is configured to rotatably disengage the first drive gear from the first reel independently from a rotatable disengagement of the second drive gear from the second reel.

15. The delivery device of claim 13, wherein the first predetermined tension limit is different than the second predetermined tension limit.

16. The delivery device of claim 1, wherein the actuator is directly connected to the first drive gear.

17. The delivery device of claim 1, wherein the tension management device is configured to adjust the predetermined tension limit.

18. The delivery device of claim 17, wherein the tension management device further comprises a switch configured to adjust the predetermined tension limit.

19. The delivery device of claim 18, wherein the switch is configured to adjust a biasing force that biases the first reel and the first drive gear together.

* * * * *